United States Patent
Bang et al.

(10) Patent No.: US 11,935,239 B2
(45) Date of Patent: Mar. 19, 2024

(54) CONTROL METHOD, APPARATUS AND PROGRAM FOR SYSTEM FOR DETERMINING LESION OBTAINED VIA REAL-TIME IMAGE

(71) Applicant: INDUSTRY ACADEMIC COOPERATION FOUNDATION, HALLYM UNIVERSITY, Chuncheon-si (KR)

(72) Inventors: Chang Seok Bang, Chuncheon-si (KR); Jae Jun Lee, Chuncheon-si (KR); Bum Joo Cho, Seoul (KR)

(73) Assignee: INDUSTRY ACADEMIC COOPERATION FOUNDATION, HALLYM UNIVERSITY, Chuncheon-si (KR)

( * ) Notice: Subject to any disclaimer, the term of this patent is extended or adjusted under 35 U.S.C. 154(b) by 0 days.

(21) Appl. No.: 18/260,245

(22) PCT Filed: Jan. 5, 2022

(86) PCT No.: PCT/KR2022/000109
§ 371 (c)(1),
(2) Date: Jul. 1, 2023

(87) PCT Pub. No.: WO2022/149836
PCT Pub. Date: Jul. 14, 2022

(65) Prior Publication Data
US 2024/0037733 A1    Feb. 1, 2024

(30) Foreign Application Priority Data
Jan. 11, 2021    (KR) .................. 10-2021-0003315

(51) Int. Cl.
*G06T 7/00*    (2017.01)
*A61B 1/00*    (2006.01)
(Continued)

(52) U.S. Cl.
CPC ...... *G06T 7/0012* (2013.01); *A61B 1/000094* (2022.02); *A61B 1/00016* (2013.01);
(Continued)

(58) Field of Classification Search
CPC .............. G06T 7/0012; G06T 2200/24; G06T 2207/10016; G06T 2207/10068;
(Continued)

(56) References Cited

U.S. PATENT DOCUMENTS 11,100,633 B2 *   8/2021   Ngo Dinh .............. G06V 20/40
11,191,423 B1 *   12/2021  Zingaretti .............. G06T 19/00
(Continued)

FOREIGN PATENT DOCUMENTS

CN    107658028 A    2/2018
CN    108695001 A    10/2018
(Continued)

OTHER PUBLICATIONS

Korean Office Action dated Aug. 22, 2022 in corresponding Korean Patent application No. 10-2021-0003315 (5 pages in Korean, 5 pages in English).
(Continued)

*Primary Examiner* — Nay A Maung
*Assistant Examiner* — Jose M Torres
(74) *Attorney, Agent, or Firm* — NSIP Law

(57) ABSTRACT

Provided is a control method for a system for determining a lesion obtained via real-time image. The control method comprises: an endoscope device obtaining a stomach endoscopy image; the endoscope device transmitting the obtained stomach endoscopy image to a server; the server determining a lesion included in the stomach endoscopy image, by inputting the stomach endoscopy image into a first artificial intelligence model; when it is determined that a lesion is detected in the stomach endoscopy image, the server obtain-
(Continued)

ing an image including the lesion and transmitting the image to a database of the server; the server determining the type of the lesion included in the image, by inputting the image into a second artificial intelligence model; and when it is determined that a lesion is detected in the stomach endoscopy image, a display device displaying a UI for guiding the location of the lesion in the stomach endoscopy image.

8 Claims, 8 Drawing Sheets

(51) Int. Cl.
*G06V 10/82* (2022.01)
*G06V 10/94* (2022.01)
*G06V 20/40* (2022.01)
*G06V 20/50* (2022.01)

(52) U.S. Cl.
CPC ............ *A61B 1/0004* (2022.02); *G06V 10/82* (2022.01); *G06V 10/945* (2022.01); *G06V 10/95* (2022.01); *G06V 20/41* (2022.01); *G06V 20/49* (2022.01); *G06V 20/50* (2022.01); *G06T 2200/24* (2013.01); *G06T 2207/10016* (2013.01); *G06T 2207/10068* (2013.01); *G06T 2207/20081* (2013.01); *G06T 2207/20084* (2013.01); *G06T 2207/30092* (2013.01); *G06T 2207/30096* (2013.01); *G06T 2207/30104* (2013.01)

(58) Field of Classification Search
CPC . G06T 2207/20081; G06T 2207/20084; G06T 2207/30092; G06T 2207/30096; G06T 2207/30104; A61B 1/000094; A61B 1/00016; A61B 1/0004; G06V 10/82; G06V 10/945; G06V 10/95; G06V 20/41; G06V 20/49; G06V 20/50
See application file for complete search history.

(56) References Cited

U.S. PATENT DOCUMENTS

| 2018/0242817 A1* | 8/2018 | Imaizumi | G06T 11/60 |
| 2020/0193236 A1* | 6/2020 | Oosake | G06V 10/454 |
| 2021/0153808 A1* | 5/2021 | Tada | G16H 50/20 |
| 2023/0037178 A1* | 2/2023 | Kamon | G06T 7/0012 |

FOREIGN PATENT DOCUMENTS

| JP | 2020-073081 A | 5/2020 |
| JP | 2020-089710 A | 6/2020 |
| JP | 2020-89711 A | 6/2020 |
| KR | 10-2015-0085943 A1 | 12/2015 |
| KR | 10-2019-0103937 A1 | 9/2019 |
| KR | 10-2058884 B1 | 12/2019 |
| KR | 10-2185886 B1 | 12/2020 |

OTHER PUBLICATIONS

Korean Notice of Allowance dated Feb. 23, 2023 in corresponding Korean Patent application No. 10-2021-0003315 (2 pages in Korean, 3 pages in English).
International Search Report dated Apr. 14, 2022 in counterpart of PCT/KR2022/000109 (4 pages in English, 3 pages in Korean).
International Preliminary Report on Patentability dated Apr. 14, 2022 in counterpart of PCT/KR2022/000109 (4 pages in English, 4 pages in Korean).
Chinese Office Action dated Nov. 9, 2023, in counterpart Chinese Patent Application No. 202280009042.4 (9 pages in English, 9 pages in Chinese).

* cited by examiner

FIG. 4

| Patient name : | | |
| Chart # : | | |
| Sex : ◯ Male ◯ Female | | |
| Year of Birth : | (Age) | |

Complete   Cancel

↶ —450
👤 —410
🖼 —420
◆ —430
⚙ —440

CONTROL METHOD, APPARATUS AND PROGRAM FOR SYSTEM FOR DETERMINING LESION OBTAINED VIA REAL-TIME IMAGE

CROSS REFERENCE TO RELATED APPLICATIONS

This application is a U.S. National Stage Application of International Application No. PCT/KR2022/000109, filed on Jan. 5, 2022, which claims the benefit under 35 USC 119(a) and 365(b) of Korean Patent Application No. 10-2021-0003315, filed on Jan. 11, 2021 in the Korean Intellectual Property Office, the entire disclosure of which is incorporated herein by reference for all purposes.

BACKGROUND

Field

The present disclosure relates to a control method, apparatus, and program for a system for determining a lesion acquired through a real-time image, and more particularly, to an endoscopic examination assisting apparatus and method for automatically detecting and determining a lesion in upper gastrointestinal endoscopy real-time images by using deep learning, and providing information on a depth of invasion into gastric wall.

Related Art

South Korea has the highest incidence rate of gastric cancer in the world, and upper gastrointestinal endoscopy examinations are widely conducted for the detection and determination of gastric cancer and its precursor lesions, which are gastric neoplasms. The determination of gastric neoplasms, including gastric cancer, is performed based on macroscopic findings by an endoscopist during an endoscopic examination. If a suspicious lesion is identified, reading the lesion is performed through a biopsy of tissue samples obtained via endoscopic biopsy. In addition, the biopsy is conducted to confirm that lesions, which are difficult to be diagnosed with bare eyes, are not malignant tumors or neoplasms.

However, the concordance rate between macroscopic findings and a biopsy result is low (when macroscopic findings by a physician does not match an actual determination), and there is also a reported inconsistency rate of 20-60% between the primary determination through a biopsy (examination of a part of the entire lesion) and a final histopathological determination of the entire specimen after surgery or endoscopic resection. This rate varies depending on the experience and skills of the physician. Therefore, due to the low initial determination accuracy, there is confusion in deciding a treatment strategy and predicting a patient's prognosis. Furthermore, if a lesion is not detected or missed during an endoscopic examination, it may directly affect the patient's prognosis. Recently, it is well known the burnout syndrome is epidemic among gastroenterologists performing endoscopic procedures. There are continuous concerns about the possibility of failing to detect lesions because it is challenging to perform comprehensive or focused examinations due to physical limitations. In other words, there is failure to meet the need for detection and determination of a gastric lesion with bare eyes.

Also, predicting a depth of invasion into the gastric wall is required to determine a treatment strategy for gastric cancer or gastric lesions. This is done mainly through microscopic tests and endoscopic ultrasound by a physician. Endoscopic resection is performed only when gastric cancer or gastric lesions are confined to the mucosa or have a submucosal invasion depth of 500 μm or less.

However, the accuracy of the macroscopic findings varies greatly depending on an individual endoscopist, and even for highly skilled experts, the accuracy of prediction of submucosal invasion using endoscopic ultrasound has been reported to be around 72-84%. Therefore, in cases where deep submucosal invasion of cancer is determined after endoscopic resection, gastric resection may be further required. For this reason, there is need for accurate determination of tumor depth in gastric cancer and gastric neoplasms.

The related art to the present disclosure is disclosed in Korean Patent No. 10-2168485.

SUMMARY

An aspect of the present disclosure provides a method for controlling a system for determining a lesion acquired through a real-time image.

Objects of the present disclosure are not limited to the aforementioned object, and other objects not mentioned will be clearly understood by those skilled in the art from the description below.

In an aspect, there is provided a control method for a system for determining a lesion through a real-time image, the method including: acquiring, by an endoscope device, a gastroscopic video; transmitting, by the endoscope device, the acquired gastroscopic video to a server; determine, by the server, a lesion included in the gastroscopic video by inputting the gastroscopic video to a first artificial intelligence model to; in response to a lesion being determined in the gastroscopic video, acquiring, by the server, an image including the lesion and transmitting the image to a database of the server; determining, by the server, the type of lesion included in the image by inputting the image to a second artificial intelligence model; and in response to a lesion being determined in the gastroscopic video, displaying, by a display device, a UI for guiding a location of the lesion in the gastroscopic video.

The determining of the lesion may include: in response to receiving a video read command from an operator while a real-time image is being taken by the endoscope device, acquiring, by the server, a plurality of images of a video taken before a predetermined time from a time when the video read command is input; determining, by the server, whether a lesion is included in the plurality of images and a type of the lesion by inputting the plurality of images to the second artificial intelligence model; in response to a determination that a lesion is included in the plurality of images, determining, by the server, whether the lesion is included in the real-time image; in response to a determination that the lesion is included in the real-time image, displaying, by the display device, a UI for guiding a location of the lesion in the real-time image.

The method may further include: in response to the endoscopic video being input to the first artificial intelligence model, determining, by the server, whether the video is a gastroscopic video; and in response to a determination that the video is not a gastroscopic video, displaying, by the display device, a UI for inputting new patient information.

The determining of whether the video is a gastroscopic video may include: acquiring, by the server, data corresponding to an average contrast of an endoscopy room where the endoscopic video is taken; and determining, by the server, whether the endoscope device is located outside a human body based on the data.

The determining of the type of lesion included in the image may include: determining, by the server, whether bleeding has occurred due to a biopsy; and in response to a determination that the bleeding has occurred, performing control not to perform lesion determination on a location of the bleeding.

The control method may further include: dividing, by the server, the endoscopic video into a plurality of frames; and in response to lesions being determined in consecutive frames equal to or greater than a preset number among the plurality of frames, determining, by the server, the lesions corresponding to the consecutive frames as a same lesion.

The displaying of the UI may include: displaying a first icon for inputting patient information, a second icon for checking an image including a determined lesion, a third icon for checking an examination result image, a fourth icon for changing a set value, and a fifth icon for returning to a real-time image; in response to receiving a user command for the first icon, displaying a first UI for inputting a patient's name, chart number, sex, and year of birth; in response to receiving a user command for the second icon, displaying a second UI for guiding a list of images including lesions; in response to receiving a user command for the third icon, displaying a third UI for guiding a list indicating results of determination of the respective lesions; in response to receiving a user command for the fourth icon, displaying a fourth UI for changing a set value; in response to receiving a user command for the fifth icon, displaying a fifth UI for displaying a real-time image; and in response to receiving a user command for one of the first icon, the second icon, the third icon, and the fourth icon while the fifth UI is displayed, displaying a UI corresponding to the first user command on a first layer.

The determining of the lesion included in the gastroscopic video may include: determining whether the determined lesion is a lesion requiring a real-time procedure; in response to the determined lesion being a lesion requiring a real-time procedure, calculating a difference between a time when the gastroscopic video is received from the endoscope device and a time when the lesion included in the gastroscopic video is determined; and in response to the difference equal to or greater than a preset value, displaying information on the lesion requiring the procedure and the difference on the fifth UI.

Other specific details of the present disclosure are included in the detailed description and drawings.

According to various embodiments of the present disclosure described above, by performing the lesion determination using an artificial intelligence model in real time, it is possible to improve the accuracy of gastric endoscopic imaging and procedure.

Effects of the present disclosure are not limited to the aforementioned effect, and other effects not mentioned will be clearly understood by those skilled in the art from the description below.

BRIEF DESCRIPTION OF THE DRAWINGS

FIGS. 4 to 6 are exemplary diagrams for explaining a user interface (UI) screen displaying method according to an embodiment of the present disclosure.

DESCRIPTION OF EXEMPLARY EMBODIMENTS

Figure 1:
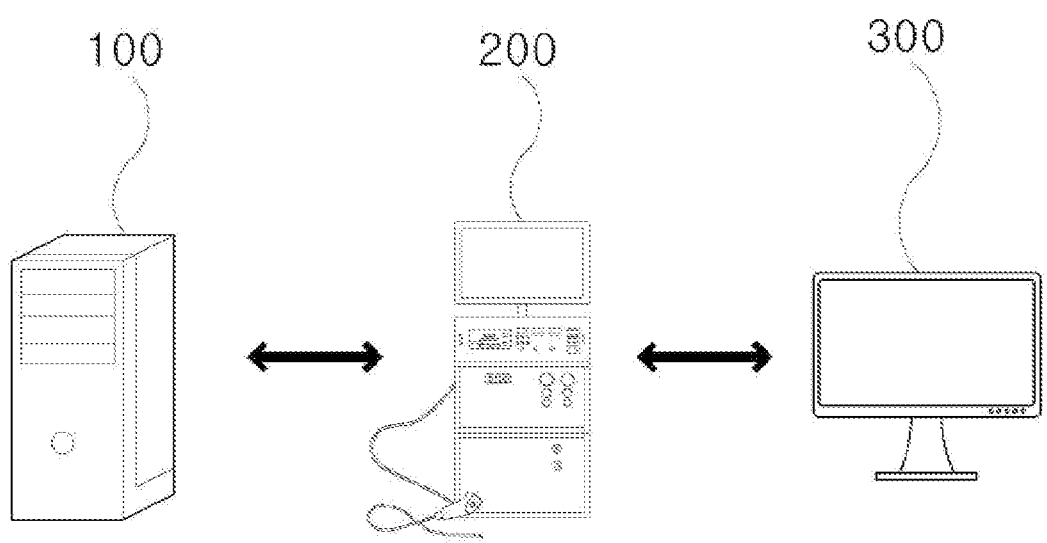
FIG. 1 is a system diagram according to an embodiment of the present disclosure.

Advantages and features of the present disclosure and a method of achieving the same should become clear with embodiments described in detail below with reference to the accompanying drawings. However, the present disclosure is not limited to the embodiments disclosed below and may be realized in various other forms. The present embodiments make the disclosure complete and are provided to completely inform one of ordinary skill in the art to which the present disclosure pertains of the scope of the disclosure. The present disclosure is defined only by the scope of the claims.

Terms used herein are for describing the embodiments and are not intended to limit the present disclosure. As used herein, the singular forms "a", "an" and "the" are intended to include the plural forms as well, unless the context clearly indicates otherwise. It will be further understood that the terms "comprises" and/or "comprising," or "includes, but is not limited to" and/or "including" when used in this specification, specify the presence of stated features, regions, integers, steps, operations, elements, and/or components, but do not preclude the presence or addition of one or more other features, regions, integers, steps, operations, elements, components, and/or groups thereof. Like reference numerals refer to like elements throughout the specification, and the term "and/or" includes, but is not limited to any and all combinations of one or more of the associated listed items. It will be understood that, although the terms first, second, and other terms may be used herein to describe various elements, these elements should not be limited by these terms. These terms are only used to distinguish one element from another. Thus, a first element may be referred to a second element without departing from the teachings of the present disclosure.

Unless otherwise defined, all terms (including technical and scientific terms) used herein have the same meanings as commonly understood by one of ordinary skill in the art to which the present device and method belongs. It will be further understood that terms, such as those defined in commonly used dictionaries, should be interpreted as having meanings that are consistent with their meaning in the context of the relevant art and/or the present description, and will not be interpreted in an idealized or overly formal sense unless expressly so defined herein.

The term "unit" in the exemplary embodiments means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of elements in use or operation in addition to the orientation depicted in the figures. For example, if an element in the figures is turned over, an element described as "below" or "beneath" other elements or features would then be oriented "above" the other elements or features. Thus, the term "below" can encompass both an orientation of above and below. An element may be otherwise oriented (rotated 90 degrees or at other orientations) and the spatially relative descriptors used herein interpreted accordingly.

In this specification, a computer means any kind of hardware device including at least one processor, and may be understood as encompassing a software configuration operating in a corresponding hardware device according to an embodiment. For example, the computer may be understood as including all of a smartphone, a tablet PC, a desktop PC, a laptop PC, and a user client and an application running in each device, but it is not limited thereto.

Hereinafter, embodiments of the present disclosure will be described in detail with reference to the accompanying drawings.

Herein, each operation will be described as being performed by a computer, but the subject of each operation is not limited thereto, and at least some of the operations may be performed in different devices depending on the embodiment.

FIG. 1 is a system diagram according to an embodiment of the present disclosure.

As shown in FIG. 1, a system for determining a lesion acquired through a real-time image may include a server 100, an endoscope device 200, and a display device 300.

In the system according to an embodiment of the present disclosure, an example of a network for sharing information between the server 100, the endoscope device 200, and the display device 300 may include, but not limited to, 3GPP (3rd Generation Partnership Project) network, LTE (Long Term Evolution) network, 5G network, WIMAX (World Interoperability for Microwave Access) network, wired and wireless Internet, LAN (Local Area Network), Wireless LAN (Wireless Local Area Network)), WAN (Wide Area Network), PAN (Personal Area Network), Bluetooth network, Wifi network, NFC (Near Field Communication) network, satellite broadcasting network, analog broadcasting network, DMB (Digital Multimedia Broadcasting) network, etc.

The server 100 is a component for obtaining an image from the endoscope device 200 and determining a gastric lesion. The server 100 according to an embodiment of the present disclosure may include an image acquisition part, a data generation part, a preprocessing part, a training part, and a lesion determination part. However, the configuration of the server 100 is not limited thereto. For example, the server 100 may further include a database for storing information.

The image acquisition part may acquire a plurality of gastric lesion images. The image acquisition part may receive a gastric lesion image from a photographing device included in the endoscope device 200. The image acquisition part may acquire an image of a gastric lesion by an endoscopic imaging device (digital camera) that is used for gastroscopy. The image acquisition part may collect white-light gastroscopic images of a pathologically confirmed lesion. Also, the image acquisition part may receive a plurality of gastric lesion images from a plurality of hospitals' image storage devices and database systems. The plurality of hospitals' image storage devices may be devices that store gastric lesion images acquired during gastroscopy in multiple hospitals.

Moreover, the image acquisition part may acquire videos (images) that are taken by varying either the angle, direction, or distance of a first area in the patient's stomach. The image acquisition part may acquire gastric lesion images in JPEG format. The gastric lesion images may be styled with a 35-degree field of view at 1280×640 pixel resolution. Meanwhile, the image acquisition part may acquire gastric lesion images from which their individual identifier information has been removed. The image acquisition part may acquire gastric lesion images where the lesion is located at the center and where the black frame area has been removed.

On the contrary, if the image acquisition part acquires images of low quality or low resolution, such as out-of-focus images, images including at least one artifact, and low-dynamic-range images, these images may be excluded. In other words, the image acquisition part may exclude images if they are not applicable to a deep learning algorithm.

The data generation part may generate a dataset by linking a plurality of gastric lesion images with patient information. The patient information may include the patient's sex, age, height, weight, race, nationality, smoking status, alcohol intake, and family history. Furthermore, the patient information may include clinical information. The clinical information may refer to all data a doctor can use when making a specific determination in a hospital. In particular, the clinical information may include electronic medical records containing personal information like sex and age, specific medical treatments received, billing information, and orders and prescriptions, which are created throughout a medical procedure. Moreover, the clinical information may include biometric data such as genetic information. The biometric data may include personal health information containing numerical data like heart rate, electrocardiogram, exercise and movement levels, oxygen saturation, blood pressure, weight, and blood sugar level.

The patient information is data that is fed into a fully-connected neural network, along with the output from the convolutional neural network architecture, from the training part to be described later, and further improvements in accuracy can be expected by feeding other information other than gastric lesion images as input into an artificial neural network.

Moreover, the data generation part may generate a training dataset and a validation dataset, for use on a deep learning algorithm. A dataset, when generated, may be classified as a training dataset required for training the artificial neural network or a validation dataset for validating information on the progress of the training of the artificial neural network. For example, the data generation part may classify gastric lesion images acquired by the image acquisition part into images to be randomly used for a training dataset and images used for a validation dataset. Also, the data generation part may use all other images, except for those used for the validation dataset, as the training dataset. The validation dataset may be randomly selected. The percentage of the validation dataset and the percentage of the training dataset may take on preset reference values. The preset reference values may be 10% for the validation dataset and 90% for the training dataset, respectively, but not limited thereto.

The data generation part may generate the training dataset and the validation dataset separately in order to avoid overfitting. For example, neural network architectures may be overfitted to the training dataset due to their learning characteristics. Thus, the data generation part may use the validation dataset to avoid overfitting of the artificial neural network.

In this case, the validation dataset may be a dataset that is not redundant with the training dataset. Since validation data is not used for building an artificial neural network, the validation data is the first data that the artificial neural network will encounter during validation. Accordingly, the validation dataset may be suitable for evaluating the performance of the artificial neural network when new images (not used for training) are fed as input.

The preprocessing part may preprocess a dataset in a way that is applicable to a deep learning algorithm. The preprocessing part may preprocess a dataset in order to enhance the recognition performance of the deep learning algorithm and minimize similarities between different patients' videos. The deep learning algorithm may be composed of two parts: a convolutional neural network architecture and a fully-connected neural network architecture.

The artificial intelligence model according to an embodiment of the present disclosure may be a modified UNet++ to which an edge smoothing algorithm is applied in UNet++ that is a modified model of UNet. In this case, the Backbone of Modified UNet++ may be DenseNet121.

Figure 2:
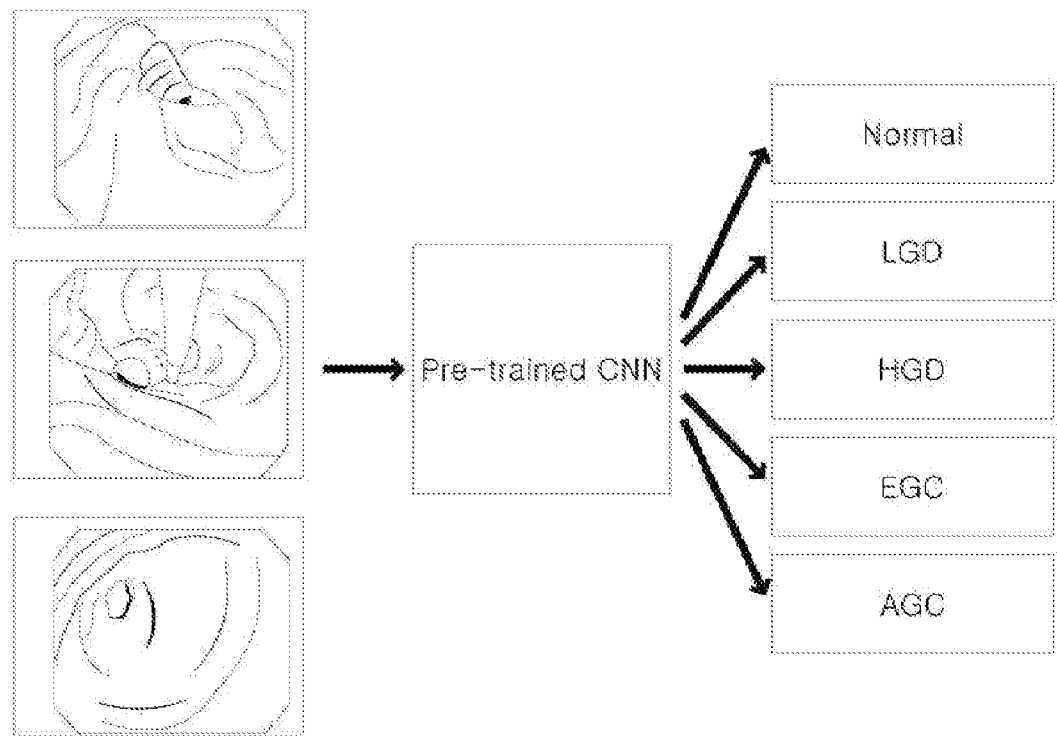
FIGS. 2 and 3 are exemplary diagrams for explaining a preprocessing method of an artificial intelligence model according to an embodiment of the present disclosure.

On the other hand, as shown in FIG. 2, the artificial intelligence model according to the present disclosure may be a 5-category classification model for advanced gastric cancer, early gastric cancer, high-grade dysplasia, low-grade dysplasia, and normal category.

In this case, the AI model may use the following parameters: a) Weight Initialization with ImageNet, b) Augmentation: Horizontal/Vertical Flip, Rotate(-10°~+10°), c) Batch Size: 6, d) Learning Rate: 4e-04, e) Epoch: 100, f) Optimizer: Adam, g) Loss Function: categorical crossentropy.

Figure 3:
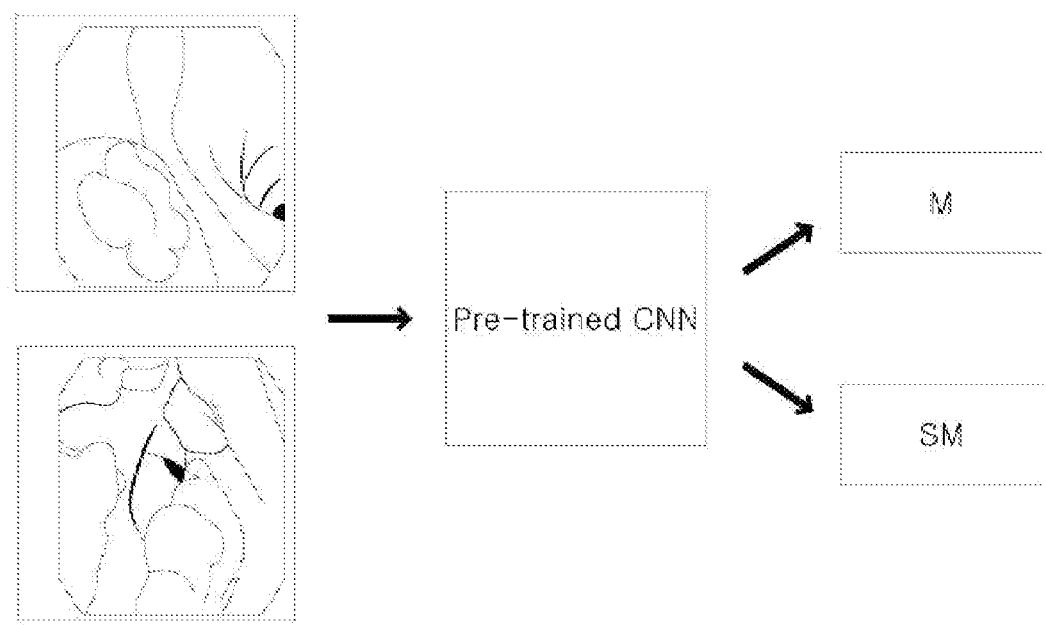

As another example, as shown in FIG. 3, the artificial intelligence model according to the present disclosure may be a 2-category classification model for determining whether a lesion is confined to the mucosa (i.e., a mucosa-confined lesion) or whether there is submucosal invasion (i.e., a submucosa-invaded lesion).

In this case, the AI model may use the following parameters: a) Augmentation: Horizontal/Vertical Flip, Rotate(-5°~+5°), Horizontal/Vertical Shift(-10%~+10%), Zoom (0.8~1.2), b) Batch Size: 2, c) Learning Rate: 1.25e-4, d) Epoch: 200, e) Dropout: 0.4, f) Learning Rate Scheduler with 0.97 decay was used.

According to various embodiments, the artificial intelligence model according to the present disclosure may be a 4-category classification model for advanced gastric cancer, early gastric cancer, dysplasia, and normal category.

The preprocessing part may include an augmentation part (not shown) for augmenting image data to increase the amount of gastric lesion image data.

According to an exemplary embodiment of the present disclosure, in the case of a deep learning algorithm including a convolutional neural network, the greater the amount of data, the better the performance. However, the amount of gastroscopic images from endoscopic examinations is much less than the amount of images from other types of examinations, and therefore the amount of gastric lesion image data collected and detected by the image acquisition part may be very insufficient for use on a convolutional neural network. Thus, the augmentation part (not shown) may perform a data augmentation process based on a training dataset. The augmentation part (not shown) may perform a data augmentation process by applying at least one of the following: rotating, flipping, cropping, and adding noise into gastric lesion images.

The preprocessing part may perform a preprocessing process in a way that corresponds to a preset reference value. The preset reference value may be arbitrarily specified by the user. Also, the preset reference value may be determined by an average value for acquired gastric lesion images. A dataset may be provided to the training part once it has undergone the preprocessing part.

The training part may build an artificial neural network by training the artificial neural network by using a preprocessed dataset as input and gastric lesion classification results as output.

According to an exemplary embodiment of the present disclosure, the training part may provide gastric lesion classification results as output by applying a deep learning algorithm consisting of two parts: a convolutional neural network architecture and a fully-connected neural network architecture. The fully-connected neural network is a neural network in which nodes are two-dimensionally interconnected horizontally and longitudinally and there are interconnections between nodes on adjacent layers but not between nodes within the same layer.

The training part may build a training model in which a convolutional neural network is trained by taking a preprocessed training dataset as input and a fully-connected neural network is trained by taking the output of the convolutional neural network as input.

According to an exemplary embodiment of the present disclosure, the convolutional neural network may extract a plurality of specific feature patterns by analyzing gastric lesion images. In this case, the extracted specific feature patterns may be used for final classification in the fully-connected neural network.

Convolutional neural networks are a type of neural network mainly used for speech recognition or image recognition. Since the convolutional neural network is constructed to process multidimensional array data, it is specialized for processing a multidimensional array such as a color image array. Accordingly, most techniques using deep learning in image recognition are based on convolutional neural networks.

The convolutional neural network CNN processes an image by partitioning it into multiple segments, rather than using the whole image as a single piece of data. This can extract local features of the image even if the image is distorted, thereby allowing the convolutional neural network CNN to deliver proper performance.

The convolutional neural network may consist of a plurality of layers. The elements of each layer may include a convolutional layer, an activation function, a max pooling layer, an activation function, and a dropout layer. The convolutional layer serves as a filter called a kernel to locally process the entire image (or a newly generated feature pattern) and extract a new feature pattern of the same size as the image. For a feature pattern, the convolutional layer may correct the values of the feature pattern through the activation function to make it easier to process them. The max pooling layer may take a sample from a gastric lesion image and reduce the size of the image by size adjustment. Although feature patterns are reduced in size as they pass through the convolutional layer and the max pooling layer, the convolutional neural network may extract a plurality of feature patterns by using a plurality of kernels. The dropout layer may involve a method in which, when training the weights of the convolutional neural network, some of the weights are not used deliberately for efficient training. Meanwhile, the dropout layer may not be applied when actual testing is performed through a training model.

A plurality of feature patterns extracted from the convolutional neural network may be delivered to the following phase, i.e., the fully-convolutional neural network, and used for classification. The convolutional neural network may adjust the number of layers. By adjusting the number of layers in the convolutional neural network to fit the amount of training data required for model training, the model may be built with higher stability.

Moreover, the training part may build a determination (training) model in which a convolutional neural network is trained by taking a preprocessed training dataset as input and a fully-connected neural network is trained by taking the output of the convolutional neural network and the patient information as input. In other words, the training part may allow preprocessed image data to preferentially enter the convolutional neural network and allow the output of the convolutional neural network to enter the fully-connected neural network. Also, the training part may allow randomly extracted features to directly enter the fully-connected neural network without passing through the convolutional neural network.

In this case, the patient information may include various information such as the patient's sex, age, height, weight, race, nationality, smoking status, alcohol intake, and family history. Furthermore, the patient information may include clinical information. The clinical information may refer to all data a doctor can use when making a specific determination in a hospital. In particular, the clinical information may include electronic medical records containing personal information like sex and age, specific medical treatments received, billing information, and orders and prescriptions, which are created throughout a medical procedure. Moreover, the clinical information may include biometric data such as genetic information. The biometric data may include personal health information containing numerical data like heart rate, electrocardiogram, exercise and movement levels, oxygen saturation, blood pressure, weight, and blood sugar level.

The patient information is data that is fed into a fully-connected neural network, along with the output of the convolutional neural network architecture, from the training part, and further improvements in accuracy can be expected by feeding the patient information as input into an artificial neural network, rather than deriving the output by using gastric lesion images alone.

For example, once training is done on clinical information in a training dataset, indicating that the incidence of cancer increases with age, the input of an age 42 or 79, along with image features, may derive a gastric lesion classification result showing that older patients with an uncertain lesion hard to classified as benign or malignant are highly likely to have cancer.

The training part may perform training by applying training data to a deep learning algorithm architecture (an architecture in which the training data is fed into the fully-connected neural network through the convolutional neural network), calculating the error between the output derived from the training data and the actual output, and giving feedback on the outputs through a backpropagation algorithm to gradually change the weights of the neural network architecture by an amount corresponding to the error. The backpropagation algorithm may adjust the weight between each node and its next node in order to reduce the output error (difference between the actual output and the derived output). The training part may derive a final determination model by training the neural networks on a training dataset and a validation dataset and calculating weight parameters.

The lesion determination part may perform a gastric lesion determination through an artificial neural network after passing a new dataset through a preprocessing process. In other words, the lesion determination part may derive a determination on new data by using the final determination model derived by the training part. The new data may include gastric lesion images based on which the user wants to make a determination. The new dataset may be a dataset that is generated by linking gastric lesion images with patient information. The new dataset may be preprocessed such that it becomes applicable to a deep learning algorithm after passing through the preprocessing process of the preprocessing part. Afterwards, the preprocessed new dataset may be fed into the training part to make a determination with respect to the gastric lesion images based on training parameters.

According to an exemplary embodiment of the present disclosure, the lesion determination part may classify a gastric lesion determination as at least one of the following categories: advanced gastric cancer, early gastric cancer, high-grade dysplasia, and low-grade dysplasia. Moreover, the lesion determination part may classify gastric lesions as cancerous or non-cancerous. Also, the lesion determination part may classify gastric lesions into two categories: neoplasm and non-neoplasm. The neoplasm category may include AGC, EGC, HGD, and LGD. The non-neoplasm category may include lesions such as gastritis, benign ulcers, erosions, polyps, or intestinal metaplasia, and epithelial tumor.

The server 100 may analyze images acquired by the endoscopic device 200 and automatically classify and determine uncertain lesions, in order to reduce side effects of an unnecessary biopsy or endoscopic excision performed to classify and determine uncertain lesions, and may allow the doctor to proceed with an endoscopic excision treatment in the case of a neoplasm (dangerous tumor).

The endoscopy device 200 may be a device used for gastroscopic examination. The endoscope device 200 may include an operation part and a body part. The endoscopic device 200 may include the body part to be inserted into the body and the operation part provided on the rear end of the body part. An imaging part for imaging the inside of the body, a lighting part for illuminating a target region, a water spray part for washing the inside of the body to facilitate imaging, and a suction part for sucking foreign materials or air from inside the body may be provided on the front end of the body part. Channels corresponding to these units (parts) may be provided inside the body part. In addition, a biopsy channel may be provided inside an insertion part, and an endoscopist may take samples of tissue from inside the body by inserting a scalpel through the biopsy channel. The imaging part (i.e., camera) for imaging the inside of the body, provided at the endoscopic device 200, may have a miniature camera. The imaging device may acquire white-light gastroscopic images.

The imaging part of the endoscopic device 200 may send and receive acquired gastric lesion images to the server 100 over a network. The server 100 may generate a control signal for controlling the biopsy unit based on a gastric lesion determination. The biopsy unit may be a unit for taking samples of a tissue from inside the body. The tissue samples taken from inside the body may determine whether the tissue is benign or malignant. Also, cancer tissue may be removed by excision of tissue from inside the body. For example, the server 100 may be included in the endoscopic device 200 which acquires gastroscopic images and takes samples of tissue from inside the body. In other words, a gastric lesion may be determined and predicted by feeding gastroscopic images, acquired in real time from the endoscopic device 200, into an artificial neural network built on training and putting them into at least one of the categories for gastric lesion determination.

According to another exemplary embodiment of the present disclosure, the endoscopic device 200 may be made in capsule form. For example, the endoscopic device 200 may be made in capsule form and inserted into a patient's body to acquire gastroscopic images. The capsule endoscopic device 200 also may provide location information which shows where it is located—either in the esophagus, the stomach, the small intestine, or the large intestine. In other words, the capsule endoscopic device 200 may be positioned inside the patient's body and provide a real-time image (image) to the server 100 over a network. In this case, the capsule endoscopic device 200 may provide information on the locations where the gastroscopic images are acquired, as well as the gastroscopic images themselves. If the determination by the server 100 is classified as at least one of the following categories: advanced gastric cancer, early gastric cancer, high-grade dysplasia, and low-grade dysplasia—that is, non-benign risky tumor, a user (doctor) may identify the location of the lesion and remove it immediately.

According to an exemplary embodiment of the present disclosure, the server 100 may perform a gastric lesion determination based on gastric lesion endoscopic images, which are acquired in real time from the endoscopic device 200 and fed into an algorithm generated by training, and the endoscopic device 200 may remove a lesion suspicious for a neoplasm by endoscopic mucosal resection or endoscopic submucosal dissection.

According to an exemplary embodiment of the present disclosure, the endoscopic device 200 may control the imaging part by using the operation part. The operation part may receive an operation input signal from the user in order that the imaging part has a target lesion within its field of view. The operation part may control the position of the imaging part based on an operation input signal inputted from the user. Also, if the field of view of the imaging part covers the target lesion, the operation part may receive an operation input signal for capturing a corresponding image and generate a signal for capturing the corresponding gastric lesion image.

According to another exemplary embodiment of the present disclosure, the endoscopic device 200 may be a capsule-type device. The capsule endoscopic device 200 may be inserted into the body of a patient and remotely operated. Gastric lesion images acquired from the capsule endoscopic device 200 may include all images acquired by video recording, as well as images of a region the user wants to capture. The capsule endoscopic device 200 may include an imaging part and an operation part. The imaging part may be inserted into a human body and controlled inside the human body based on an operation signal from the operation part.

The display device 300 may include, for example, a liquid crystal display LCD, a light-emitting diode (LED) display, an organic light-emitting diode (OLED) display, or a microelectromechanical (MEMS) display. The display device 300 may present the user gastroscopic images acquired from the endoscopic device 200 and information on a gastric lesion determination made by the server 100. The display device 300 may include a touchscreen—for example, it may receive a touch, gesture, proximity, or hovering input using an electronic pen or a part of the user's body. The display device 300 may output gastroscopic images acquired from the endoscopic device 200. Also, the display device 300 may output gastric lesion determination results.

According to another exemplary embodiment of the present disclosure, the endoscopic device 200 may include an operation part, a body part, a processor, a lesion location acquisition part, and a display.

In this case, the endoscopy device 200 includes an artificial intelligence model and may determine a lesion. Specifically, in order to prevent interference with real-time gastroscopic examination due to a time difference that occurs when the artificial intelligence model determines a lesion, an algorithm related to detection possibly interfering with an examiner may be performed by the endoscopy device 200 and an algorithm related to the remaining preprocessing and reading may be performed by the server 100.

The operation part may be provided on the rear end of the body part and manipulated based on information inputted by the user. The operation part is a part that is gripped by an endoscopist, with which the body part to be inserted into the patient's body. Also, the operation part allows for manipulating the operation of a plurality of units required for an endoscopic procedure the body part contains. The operation part may include a rotary processor. The rotary processor may include a part that functions to generate a control signal and provides rotational force (such as in a motor). The operation part may include buttons for manipulating the imaging part (not shown). The buttons are used to control the position of the imaging part (not shown), by which the user may change the position of the body part upward, downward, to the left, to the right, forward, backward, and so forth.

The body part is a part that is inserted into the patient's body, and may contain a plurality of units. The plurality of units may include at least one of an imaging part (not shown) for imaging the inside of the patient's body, an air supply unit for supplying air into the body, a water supply unit for supplying water into the body, a lighting unit for illuminating the inside of the body, a biopsy unit for sampling a portion of tissue in the body or treating the tissue, and a suction unit for sucking air or foreign materials from inside the body. The biopsy unit may include a variety of medical instruments, such as scalpels, needles, and so on, for sampling a portion of tissue from a living organism, and the scalpels and needles in the biopsy unit may be inserted into the body through a biopsy channel by the endoscopist to sample cells in the body.

The imaging part (not shown) may hold a camera of a size equivalent to the diameter of the body part. The imaging part (not shown) may be provided on the front end of the body part and take gastric lesion images and provide the taken gastric lesion images to the lesion determination part and the display over a network.

The processor may generate a control signal for controlling the operation of the body part based on user input information provided from the operation part and the determination results of the server 100. Upon receiving an input from the user made by selecting one of the buttons on the operation part, the processor may generate a control signal for controlling the operation of the body part to correspond to the selected button. For example, if the user selects the forward button for the body part, the processor may generate an operation control signal to enable the body part to move forward inside the patient's body at a constant speed. The body part may move forward inside the patient's body based on a control signal from the processor.

Also, the processor may generate a control signal for controlling an operation of an imaging part (not shown). The control signal for controlling the operation of the imaging part (not shown) may be a signal for allowing the imaging part (not shown) positioned in a lesion area to capture a gastric lesion image. In other words, if the user wishes to use the imaging part (not shown) positioned in a specific lesion area to acquire an image based on the operation part, the user may click on a capture button. The processor may generate a control signal to allow the imaging part (not shown) to acquire an image in the lesion area based on input information provided from the operation part. The processor may generate a control signal for acquiring a specific lesion gastric image from a video being taken the imaging part (not shown).

Additionally, the processor may generate a control signal for controlling the operation of the biopsy unit for sampling a portion of tissue in the patient's body based on the determination results of the server 100. If the determination by the server 100 is classified as at least one of the following categories: advanced gastric cancer, early gastric cancer, high-grade dysplasia, and low-grade dysplasia, the processor may generate a control signal for controlling the operation of the biopsy unit to perform an excision. The biopsy unit may include a variety of medical instruments, such as scalpels, needles, and so on, for sampling a portion of tissue from a living organism, and the scalpels and needles in the biopsy unit may be inserted into the body through a biopsy channel by the endoscopist to sample cells In the body. Also, the processor may generate a control signal for controlling the operation of the biopsy unit based on a user input signal provided from the operation part. The user may perform the operation of sampling, excising, or removing cells inside the body by using the operation part.

According to an exemplary embodiment of the present disclosure, the lesion location acquisition part may generate gastric lesion information by linking the gastric lesion images provided from the imaging part (not shown) with location information. The location information may be information on the current location of the body part inside the body. In other words, if the body part is positioned at a first point on the stomach of the patient's body and a gastric lesion image is acquired from the first point, the lesion location acquisition part may generate gastric lesion information by linking this gastric lesion image with the location information.

The lesion location acquisition part may provide the user (doctor) with the gastric lesion information generated by linking the acquired lesion gastric lesion images with the location information. By providing the user with the determination results of the lesion determination part and the gastric lesion information of the gastric lesion location acquisition part through the display, the risk of excision somewhere else other than the target lesion may be avoided when an excision treatment or surgery is performed on the target lesion.

In addition, if the biopsy unit is not positioned in the target lesion based on the location information provided from the lesion location acquisition part, the processor may generate a control signal for controlling the position of the biopsy unit.

Since the server 100 generates a control signal for controlling the biopsy unit and samples or removes cells from inside the body, tissue examinations can be made much faster. Besides, the patient may be treated quickly since cells determined as cancer can be removed immediately during an endoscopic determination procedure.

Hereinafter, the operation flow of the present disclosure will be discussed briefly based on what has been described in detail above.

Figure 7:
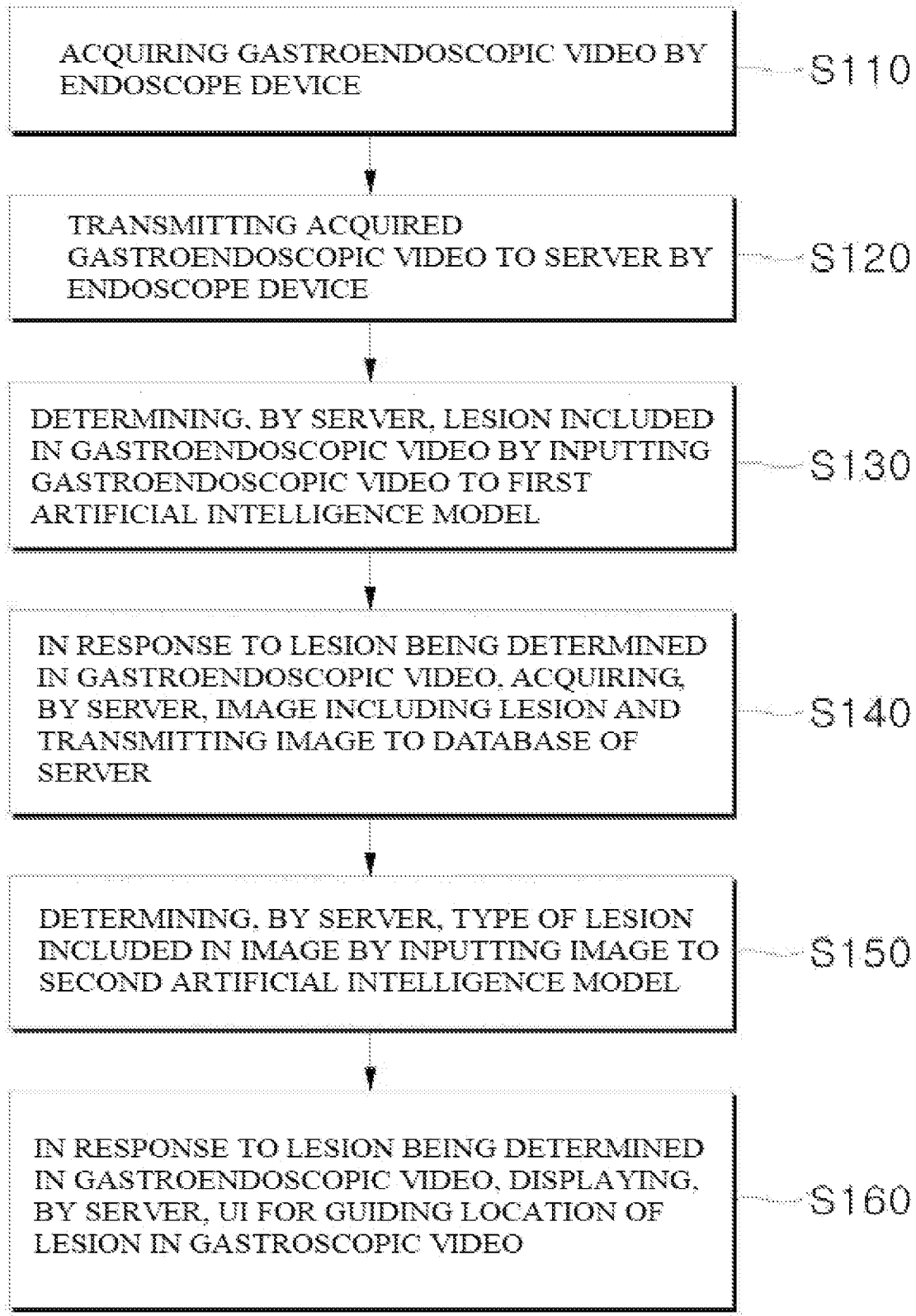
FIG. 7 is a flow chart according to an embodiment of the present disclosure.

Specifically, as shown in FIG. 7, in operation S110, the endoscopic device 200 may acquire a gastroscopic video.

In operation S120, the endoscope device 200 may transmit the acquired gastroscopic video to the server 100.

In operation S130, the server 100 may determine a lesion included in the gastroscopic video by inputting the gastroscopic video to a first artificial intelligence model.

In one embodiment, if a video read command is received from an operator while a real-time image is being captured by the endoscope device 200, the server 100 may acquire a plurality of images of a video acquired before a predetermined time from a time when the video read command is input.

Specifically, even in a case where the server 100 does not determine any lesion, the server 100 may receive a video read command from the operator if the operator finds a suspicious image.

In this case, the video read command may be a voice command. For example, when the operator speaks a voice of "read a video," the endoscope device 200 may recognize the corresponding command as a video read command and transmit a control signal for video reading to the server 100. In another example, the video read command may be an operation of pushing a preset button included in the endoscope device 200 or an operation of touching a specific UI of the display device 300.

Upon receiving the video read command, the server 100 may acquire a plurality of image frames of a video acquired before a predetermined time from the time when the video read command is input, and may perform a lesion determination on the corresponding frames.

In one embodiment, the server 100 may input a plurality of images to a third artificial intelligence model, and determine whether a lesion is included in the plurality of images and a type of the lesion.

In this case, the first artificial intelligence model and the second artificial intelligence model may be lightweight artificial intelligence models for outputting a fast result, and the third artificial intelligence model may be an artificial intelligence model for obtaining an accurate result. That is, in order to assist gastric endoscopy in real time, the first artificial intelligence model and the second artificial intelligence model capable of deriving fast results may be used, and when there is a doctor's video read command, the third artificial intelligence model requiring a long time but capable of deriving an accurate result may be used.

Thereafter, when it is determined that a lesion is included in the plurality of images, the server 100 may determine whether the lesion is included in the real-time image.

When the lesion is included, the server 100 may display a UI for guiding the location of the lesion in the real-time image.

In operation S140, when a lesion is determined in a gastroscopic video, the server 100 may acquire an image including the lesion and transmit the image to the database of the server 100.

In one embodiment, an image including a lesion stored in a database may be checked in a second UI displayed through a second icon, as will be described later.

In operation S150, the server 100 may determine the type of the lesion included in the image by inputting the image to the second artificial intelligence model.

In one embodiment, a detection algorithm applying YOLO_v3 and EfficientNet may be applied to the second artificial intelligence model. The second artificial intelligence model may recognize a lesion, remove a patient text and light reflection from the image including the lesion, read the type of the lesion, and display a result on the display device 300 in real time during the examination.

In one embodiment, the server 100 may determine whether bleeding has occurred due to a biopsy.

Specifically, the server 100 may include a fourth artificial intelligence model for detecting bleeding. The server 100 may input video images to the fourth artificial intelligence model before inputting the video images to the first artificial intelligence model and the second artificial intelligence model.

When it is determined that bleeding has occurred, the server 100 may not perform a lesion determination on a location where bleeding has occurred.

That is, when it is determined that bleeding has occurred in the video images input to the fourth artificial intelligence model, the server 100 may not input the corresponding video images to the first artificial intelligence model and the second artificial intelligence model, and only when it is not determined that bleeding has occurred in the video images input to the fourth artificial intelligence model, the server 100 may input the corresponding video images to the first artificial intelligence model and the second artificial intelligence model to perform a lesion determination.

In operation S160, when a lesion is determined in a gastroscopic video, the server 100 may display a UI for guiding the location of the lesion in the gastroscopic video. In this case, the UI for guiding the location of the lesion may be displayed by the display device 300.

Figure 5:
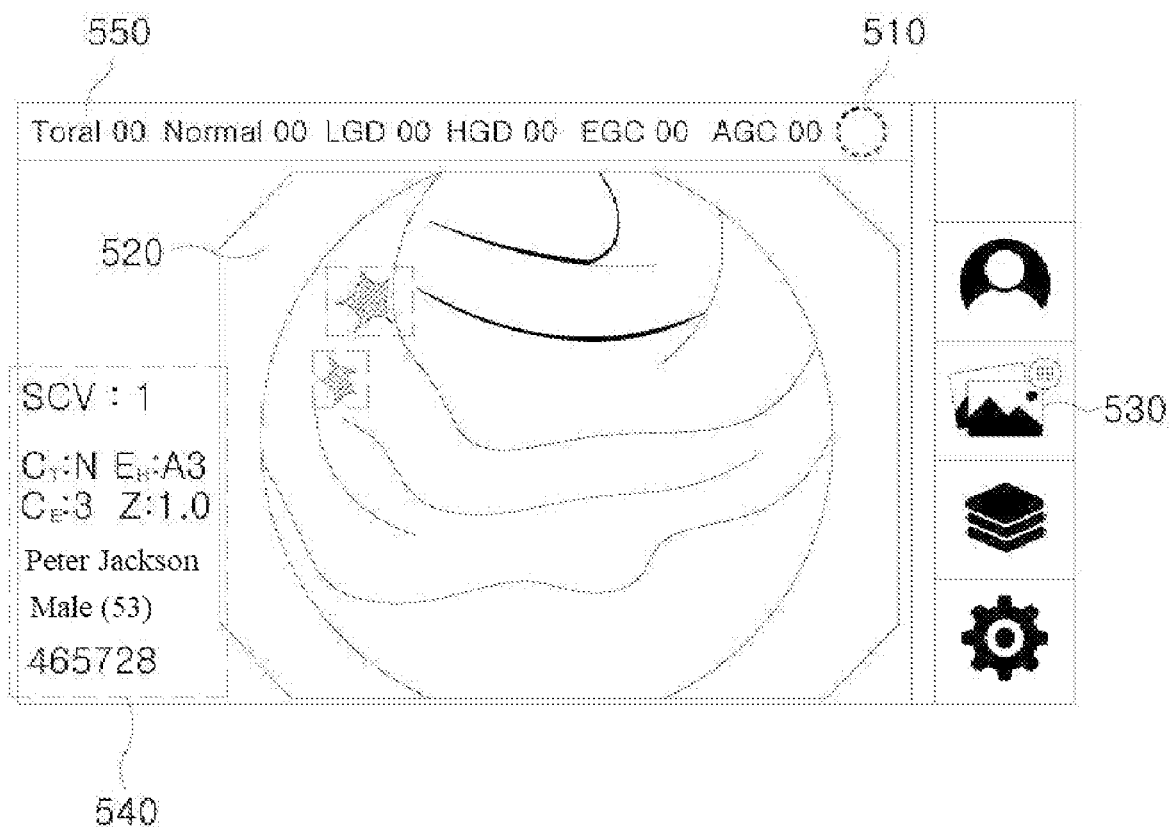

Specifically, as shown in FIGS. 4 and 5, a first icon 410 for inputting patient information, a second icon 420 for checking an image including the determined lesion, a third icon 430 for checking an examination result image, a fourth icon 440 for changing a set value, and a fifth icon 450 for returning to a real-time image may be displayed.

The first icon 410 is an icon for inputting patient information. As shown in FIG. 4, when a user command for the first icon 410 is input, the display device 100 may display a first UI for inputting a patient's name, chart number, sex, and year of birth.

The patient information may be modified even while endoscopy is in progress. Furthermore, when the first UI is displayed on the display device 300, the first icon may be highlighted in a different color from other icons, and a user command may not be input through the first icon.

Meanwhile, information may be entered to only some of a plurality of input windows included in the first UI. That is, even if information is not entered in all of the plurality of input windows, gastroscopy may be performed.

At this point, the year of birth may be entered only as a number, such as "1988" or "88", and only any year before the present time may be entered. According to various embodiments, as for the year of birth, it is possible to enter only a year prior to a preset range from the present time.

Meanwhile, the year of birth may be entered only within a predetermined range based on the present time. For example, if the present time is 2020, it is not possible to enter a year prior to the year of 1820 earlier a preset number of years (e.g., 200 years) from the present time. When a year of birth out of the range is entered, the display device 300 may output a warning message such as "Please check the year of birth."

Meanwhile, in a case where the endoscopy is in progress or in a case where insufficient patient information is input although the endoscopy is completed, the server 100 may perform indexing on the endoscopy. The case in which insufficient patient information is input may indicate a case where it cannot be distinguished from other endoscopic results. For example, in a case where only the patient's name or birth information is input but the endoscopy of the patient with the same patient name or birth information has been performed or is scheduled to be performed, the server 100 may perform indexing in order to distinguish the same patient's data. For example, when patient information is insufficient, the server 100 may generate a random chart number and add the random chart number to the patient information. The random chart number generated by the server 100 may have a different format or be displayed in a different color than a normally recorded chart number.

In one embodiment, when a user command is input through a complete icon or a cancel icon displayed on the first UI, the display device 300 may display a fifth UI for displaying a real-time image.

The second icon is an icon for checking an image stored in the database of the server 100.

When a user command for the second icon is input, the display device 300 may display a second UI for guiding an image list including lesions.

In one embodiment, the second icon may display the number of image lists together. When the number of image lists exceeds a preset number (e.g., 99), only the preset number (e.g., 99) may be displayed together with the second icon.

The third icon is an icon for displaying a determination result for each lesion.

Figure 6:
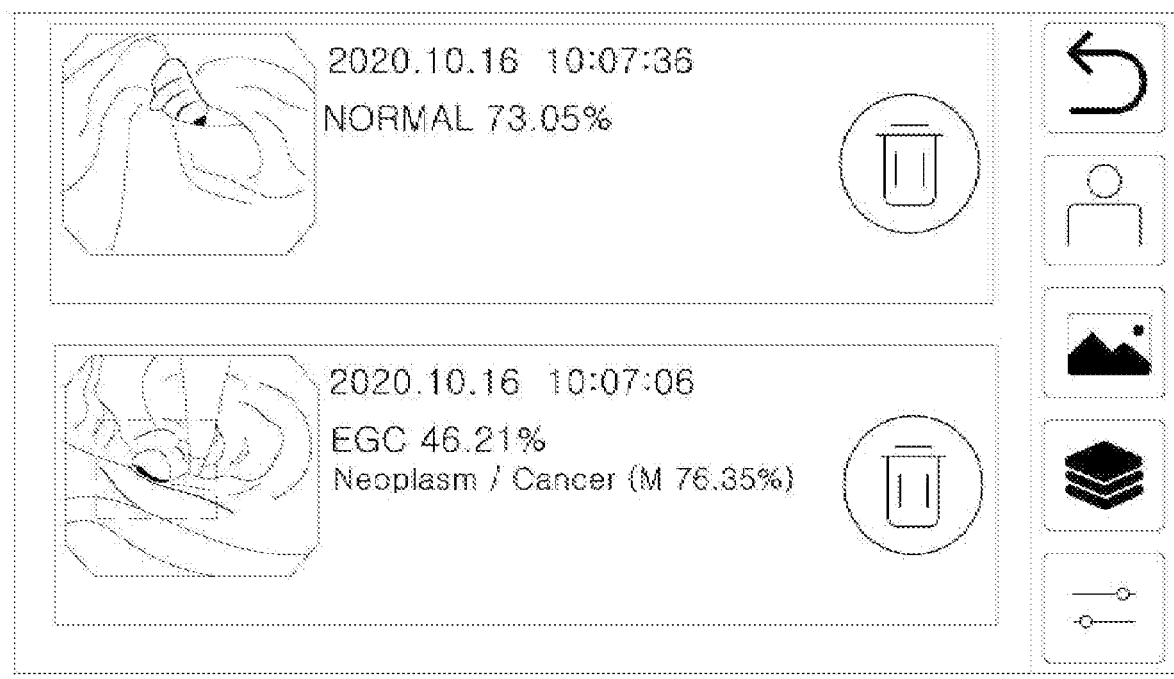

When a user command for the third icon is input, the display device 300 may display a third UI for guiding a list of determination results for respective lesions, as shown in FIG. 6.

The fourth icon is an icon for changing a set value.

When a user command is input through the fourth icon, a fourth UI for changing a set value may be displayed.

The fifth icon is an icon for returning to a real-time image.

When a user command is input through the fifth icon, the display device 300 may display a fifth UI for displaying a real-time image.

In one embodiment, when a first user command for one of the first icon, the second icon, the third icon, and the fourth icon is input while the fifth UI is displayed, the display device 300 may a UI corresponding to the first user command on a first layer.

However, even in this case, the server 100 and the display device 300 may detect a video screen in real time. To this end, the first to fourth UIs may be implemented on layers different from the fifth UI.

Meanwhile, as shown in FIG. 5, while the fifth UI is displayed, the display device 300 may display a sixth icon 510, a seventh icon 520, an eighth icon 530, a ninth icon 540, and a tenth icon 550.

The sixth icon 510 may be generated when an analysis of a lesion is in progress in the server 100. When the sixth icon 510 is displayed on the fifth UI, the operator may determine that a suspicious part exists and the server 100 is reading the corresponding part.

The seventh icon 520 is an icon for displaying a location and state of a lesion when the server 100 acquires the lesion in an image. The seventh icon may be generated to correspond to a size of the lesion, and may be displayed in a different color according to the state of the lesion. For example, it may be displayed in green for a normal state, yellow for LGD, dark yellow for HGD, orange for EGC, and red for AGC.

As described above, the eighth icon 530 may be associated with displaying the number of image lists.

The ninth icon 540 is a component for displaying patient information acquired through the first UI. In this case, the patient information may include a patient's name, sex, age, and chart information, and when patient information is not input, it may be displayed as "-".

The tenth icon 550 is a component for displaying the number of lesions determined during the endoscopy. When the number of images including suspicious lesions is added, the numbers displayed on the tenth icon 550 may be changed.

In this case, while the fifth UI is displayed, the fifth icon 450 may not be displayed.

Meanwhile, according to various embodiments of the present disclosure, the server 100 may determine whether a determined lesion is a lesion that requires a real-time procedure.

Specifically, when gastroscopy is performed, there is a need for a procedure to be performed along with the determination of the lesion. Accordingly, when determining a type of lesion, the server 100 may also determine whether the determined lesion is an operable lesion.

Thereafter, when the determined lesion is a lesion requiring a real-time procedure, the server 100 may calculate a difference between a time at which a gastroscopic video is received from the endoscope device 200 and a time at which a lesion included in the gastroscopic video is determined.

When the difference is equal to or greater than a preset value, the display device 300 may display information on the lesion requiring a treatment and the difference on the fifth UI.

That is, while the artificial intelligence model determines whether an image of the gastroscopic video includes a lesion, the operator may pass a previously identified area, so the server 100 may calculate a difference between a time at which a gastroscopic video is received and a time at which a lesion included in the gastroscopic video is determined and may inform the operator of the difference, so that a procedure on the lesion can be performed in real time during the gastroscopy.

Meanwhile, according to various embodiments of the present disclosure, when an endoscopic video is input to the first artificial intelligence model, the server 100 may determine whether the video is a gastroscopic video.

Thereafter, if the video is not a gastroscopic video, the server 100 may display a UI for inputting new patient information.

Alternatively, when the video is not a gastroscopic video, the server 100 may determine that a previous gastroscopic video is completed and the gastroscopy for a new patient has started, and then may display a video separately from the previously captured gastroscopic video.

Through the above-described method, the server 100 may classify a gastroscopic video according to a patient even when patient information is not input.

Specifically, the server 100 may acquire one class for a part other than the stomach by extracting an image including the esophagus and an image of the tongue in the patient's mouth from the gastroscopic video. Furthermore, the server 100 may acquire an image of the inside of the stomach as another class. The server 100 may train each of the acquired two classes using a two-category classification artificial intelligence algorithm.

In one embodiment, even in a case where the server 100 receives a read request for an image, a lesion determination may not be performed if it is determined that an image requested to read is not a part of the stomach according to a result of reading by the two-category classification artificial intelligence algorithm.

In yet another embodiment, the server 100 may acquire data corresponding to the average contrast of an endoscopy room where an endoscopic video is taken, and may determine whether the endoscope device 200 is located outside the human body based on the acquired data. Specifically, the server 100 may determine whether an image acquired by the endoscope device 200 is captured outside the human body based on the illuminance, chroma, and contrast information of the image acquired by the endoscope device 200. Specifically, the server 100 may acquire an average contrast value of an endoscopy room environment and compare the acquired average contrast value with a contrast value of an image acquired through the endoscope device 200 to determine that the captured image is captured outside the human body. For example, when an image acquired through the endoscope device 200 falls within in a specific brightness range, the server 100 may determine the image as an image captured outside the human body and turn off an artificial intelligence algorithm system.

According to various embodiments of the present disclosure described above, even in a case where a patient name is not input, the server 100 may automatically identify and recognize a patient and store a reading result in a storage device when another patient's endoscopy starts after the endoscopy of one patient ends.

Furthermore, the server 100 may automatically recognize and identify the esophagus connected to the stomach, mouth, and external parts of the human body from an endoscopic video not to perform artificial intelligence reading on the corresponding parts, thereby utilizing the resources of the server 100 only for the detection and determination of a lesion.

Meanwhile, according to another embodiment of the present disclosure, the server 100 may divide an endoscopic video into a plurality of frames.

Thereafter, if lesions are determined in consecutive frames equal to or greater than a predetermined number among the plurality of frames, the server 100 may determine the lesions corresponding to the consecutive frames as the same lesion.

Specifically, when lesion reading is performed on the same site in the plurality of image frames included in the gastroscopic video, the server 100 may determine corresponding lesions as the same lesion. The server 100 may acquire a lesion class (e.g., LGD) most frequently detected in image frames corresponding to the same lesion as a determined lesion.

Meanwhile, according to another embodiment of the present disclosure, the server 100 may determine whether bleeding has occurred due to a biopsy during an endoscopy.

When bleeding has occurred, the server 100 may not determine an image with the bleeding as a lesion. Specifically, the server 100 may train on multiple images with bleeding as training data, thereby enabled to distinguish the multiple images from images related to a gastric lesion.

In another embodiment, the server 100 may detect and remove various noises other than lesions found during gastroscopy. For example, when a patient text is detected on a gastroscopic screen, the server 100 may remove the detected patient text. In yet another example, when screen reflections caused by the interaction of air released from the endoscope device and the gastric fluid is detected, the server 100 may compensate for the reflections not to recognize the same. In yet another example, the server 100 may pre-store data on a biopsy instrument configured separately from the gastric endoscopy device 200 and, when the biopsy instrument is captured, an image thereof may be excluded from lesion determination. In yet another example, the server 100 may perform color correction on an image captured by the endoscope device 200.

For example, the server 100 may read only an input video by recognizing and removing all patient text through a partitioning artificial intelligence algorithm, or the server 100 may distinguish the reflected light from the endoscope device 200 by quantifying the average brightness value of a corresponding image and may control not to read the corresponding image despite receipt of a read request if a brightness value exceeds or falls below a certain threshold. Furthermore, when an external instrument such as a biopsy instrument is photographed, the server 100 may recognize the external instrument with a detection algorithm modified from YOLO_v3 and may control not to read a corresponding image despite receipt of a read request.

Meanwhile, as shown in FIG. 5, in order to prevent the operator from forgetting to view the artificial intelligence device screen or missing a detected lesion during the gastroscopy, the server 100 may display the seventh icon 520 on the display device 300 when a lesion previously detected by the server 100 reappears in the video, so that the operator can be alerted and pay attention. Furthermore, when a lesion is detected, the server 100 may immediately generate a computer notification sound and display an icon in color preset for each lesion on the UI of the display device 300.

Specifically, in a case where RGB consistency between frames is equal to or exceeds a certain threshold or falls below the certain threshold, the server 100 may maintain the location of a detected lesion in a previous frame even if no lesion is detected in a current frame. In this case, the location of the lesion may be displayed in real time in a rectangular shape, such as the seventh icon 520. Meanwhile, if no lesion is detected, the seventh icon 520 may be removed.

Meanwhile, among AI models according to the present disclosure, the maximum overall accuracy for classifying into five categories including advanced gastric cancer, early gastric cancer, dysplasia, and normal category, is 89.67%, and in this case, the sensitivity is 98.62%, and the specificity is 85.28%. The maximum overall accuracy for classifying into five categories including advanced gastric cancer, early gastric cancer, high-grade dysplasia, low-grade dysplasia, and normal category, is 77%, and in this case, the sensitivity is 85.56%, and the specificity is 94.17%. The maximum overall accuracy for classifying into two categories including a mucosa-confined lesions and a submucosa-invaded lesion, is 89.9% and, in this case, the sensitivity is 93.13%, and the specificity is 89.08%.

Figure 8:
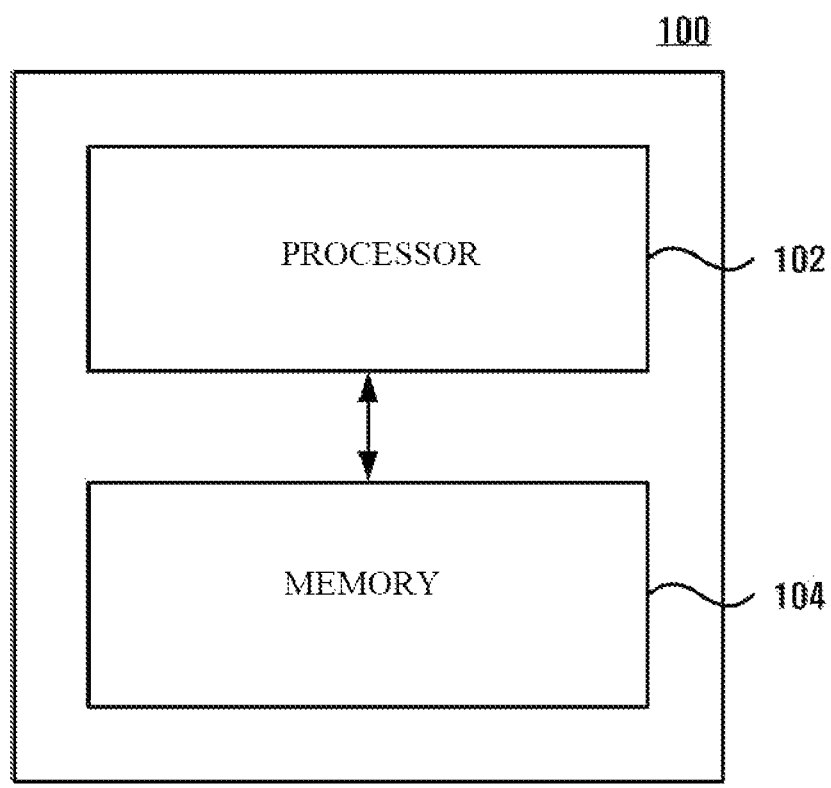
FIG. 8 is a diagram illustrating a configuration of an apparatus according to an embodiment of the present disclosure.

FIG. 8 is a diagram illustrating a configuration of a device according to an embodiment.

A processor 102 may include one or more cores (not shown) and a graphic processor (not shown), and/or a connection channel (e.g., a bus) for transmitting and receiving signals to and from other components.

The processor 102 according to an embodiment of the present disclosure executes one or more instructions stored in a memory 104 to implement the method described with respect to FIG. 7.

For example, the processor 102 may acquire new training data by executing one or more instructions stored in memory, may perform a test on the acquired new training data using a trained model, extract first training data in which the labeled information is obtained, as a result of the test, with accuracy equal to or greater than a predetermined first reference value, delete the extracted first training data from the new training data, and retrain the trained model using the new training data from which the extracted training data is deleted.

Meanwhile, the processor 102 may further include a random access memory (RAM) (not shown) or a read-only memory (ROM) (not shown) for temporarily and/or permanently storing signals (or data) processed inside the processor 102. In addition, the processor 102 may be implemented in the form of a system on chip (SoC) including at least one of a graphics processing part, a RAM, and a ROM.

The memory 104 may store programs (one or more instructions) for processing and control of the processor 102. The programs stored in the memory 104 may be divided into a plurality of modules according to their functions.

Steps of the method or algorithm described with reference to the embodiment of the present disclosure may be directly implemented in hardware, in software modules executed by hardware, or in a combination thereof. The software module may reside in a random access memory (RAM), a read only memory (ROM), an erasable programmable ROM (EPROM), an electrically erasable programmable ROM (EEPROM), a flash memory, a hard disk, a removable disk, a CD-ROM, or in any form of computer readable recording medium known in the art to which the present disclosure pertains.

The components of the present disclosure may be implemented as a program (or application) to be executed in combination with a computer, which is hardware, and stored in the medium. The components of the present disclosure may be implemented as software programming or software components, and similarly, the embodiments may be implemented in programming or scripting languages such as C++, Java, assembler, or the like including various algorithms implemented as data structures, processes, routines, or combinations of other programming structures. Functional aspects may be implemented in an algorithm running on one or more processors, Although the embodiments of the present disclosure have been described with reference to the accompanying drawings, but the ordinarily skilled in the art to which the present disclosure belongs can understand that the present disclosure can be carried out in other specific forms without changing technical spirit or essential features. Therefore, it should be understood that the embodiments described above are illustrative in all respects and are not restrictive.

What is claimed is:

1. A control method for a system for determining a lesion through a real-time image, the method comprising:
acquiring, by an endoscope device, a gastroscopic video;
transmitting, by the endoscope device, the acquired gastroscopic video to a server;

determine, by the server, a lesion included in the gastroscopic video by inputting the gastroscopic video to a first artificial intelligence model to;

in response to a lesion being determined in the gastroscopic video, acquiring, by the server, an image including the lesion and transmitting the image to a database of the server;

determining, by the server, the type of lesion included in the image by inputting the image to a second artificial intelligence model; and in response to a lesion being determined in the gastroscopic video, displaying, by a display device, a UI for guiding a location of the lesion in the gastroscopic video, wherein the determining of the lesion comprises:

in response to receiving a video read command from an operator while a real-time image is being taken by the endoscope device, acquiring, by the server, a plurality of images of a video taken before a predetermined time from a time when the video read command is input;

determining, by the server, whether a lesion is included in the plurality of images and a type of the lesion by inputting the plurality of images to the second artificial intelligence model;

in response to a determination that a lesion is included in the plurality of images, determining, by the server, whether the lesion is included in the real-time image;

in response to a determination that the lesion is included in the real-time image, displaying, by the display device, a UI for guiding a location of the lesion in the real-time image, wherein the determining of the type of lesion included in the image comprises:

determining, by the server, whether bleeding has occurred due to a biopsy; and in response to a determination that the bleeding has occurred, performing control not to perform lesion determination on a location of the bleeding.

2. The control method of claim 1, further comprising:

in response to the endoscopic video being input to the first artificial intelligence model, determining, by the server, whether the video is a gastroscopic video; and in response to a determination that the video is not a gastroscopic video, displaying, by the display device, a UI for inputting new patient information.

3. The control method of claim 2, wherein the determining of whether the video is a gastroscopic video comprises:

acquiring, by the server, data corresponding to an average contrast of an endoscopy room where the endoscopic video is taken; and determining, by the server, whether the endoscope device is located outside a human body based on the data.

4. The control method of claim 1, further comprising:

dividing, by the server, the endoscopic video into a plurality of frames; and in response to lesions being determined in consecutive frames equal to or greater than a preset number among the plurality of frames, determining, by the server, the lesions corresponding to the consecutive frames as a same lesion.

5. The control method of claim 1, wherein the displaying of the UI comprises:

displaying a first icon for inputting patient information, a second icon for checking an image including a determined lesion, a third icon for checking an examination result image, a fourth icon for changing a set value, and a fifth icon for returning to a real-time image;

in response to receiving a user command for the first icon, displaying a first UI for inputting a patient's name, chart number, sex, and year of birth;

in response to receiving a user command for the second icon, displaying a second UI for guiding a list of images including lesions;

in response to receiving a user command for the third icon, displaying a third UI for guiding a list indicating results of determination of the respective lesions;

in response to receiving a user command for the fourth icon, displaying a fourth UI for changing a set value; and in response to receiving a user command for the fifth icon, displaying a fifth UI for displaying a real-time image; and in response to receiving a user command for one of the first icon, the second icon, the third icon, and the fourth icon while the fifth UI is displayed, displaying a UI corresponding to the first user command on a first layer.

6. The control method of claim 5, wherein the determining of the lesion included in the gastroscopic video comprises:

determining whether the determined lesion is a lesion requiring a real-time procedure;

in response to the determined lesion being a lesion requiring a real-time procedure, calculating a difference between a time when the gastroscopic video is received from the endoscope device and a time when the lesion included in the gastroscopic video is determined; and in response to the difference equal to or greater than a preset value, displaying information on the lesion requiring the procedure and the difference on the fifth UI.

7. An apparatus for performing the method of claim 1, the apparatus comprising:

a memory configured to store one or more instructions; and a processor configured to execute the one or more instructions stored in the memory, wherein the processor executes the one or more instructions.

8. A computer program stored in a computer-readable recording medium to perform the method of claim 1 in combination with a computer.

\* \* \* \* \*